United States Patent [19]
Iida et al.

[11] Patent Number: 4,518,591
[45] Date of Patent: May 21, 1985

[54] HYPOGLYCEMIC AGENTS

[75] Inventors: Seiu Iida, Tsukui; Tomio Inokuchi, Sagamihara; Hiroaki Munakata, Yokohama, all of Japan

[73] Assignee: Mitsubishi Chemical Industries, Ltd., Tokyo, Japan

[21] Appl. No.: 346,091

[22] Filed: Feb. 5, 1982

Related U.S. Application Data

[63] Continuation of Ser. No. 114,326, Jan. 22, 1980, abandoned.

[30] Foreign Application Priority Data

Feb. 13, 1979 [JP] Japan .................................. 54-15303

[51] Int. Cl.³ ............................................ A61K 35/78
[52] U.S. Cl. .................................................. 424/195.1
[58] Field of Search ......................................... 424/195

[56] References Cited

PUBLICATIONS

Park–Chem Abst. 80; 24824z.

Primary Examiner—Allen J. Robinson
Assistant Examiner—John W. Rollins
Attorney, Agent, or Firm—Wegner & Bretschneider

[57] ABSTRACT

There are disclosed an acylated derivative of water extract of *Anemarrhenae rhizoma* which is so-called "Chimo", and a hypoglycemic agent containing the above acylated derivative of water extract of Chimo as an active ingredient.

4 Claims, 6 Drawing Figures

HYPOGLYCEMIC AGENTS

This application is a continuation of application Ser. No. 114,326, filed Jan. 22, 1980, now abandoned.

BACKGROUND OF THE INVENTION

1. Field of the Invention

This invention relates to a new hypoglycemic agent obtained from a crude drug, Anemarrhenae rhizoma which is so-called "Chimo".

2. Description of the Prior Art

Chimo, Anemarrhenae rhizoma which has been used as a crude drug is a bulb of "Anemarrhena asphodeloides Bunge" which is a plant of the Liliaceae family growing wild in China.

It has been known that an aqueous extract of Chimo, when administered orally, give hypoglycemic effect on normal or alloxan diabetic rabbits, and alloxan diabetic or anti-insulin serum diabetic mice (Masayasu Kimura, "Nippon Rinsho" 25, 2841 (1967)). Several synthetic oral drugs and insulin have been used so far as hypoglycemic agents in treating diabetes mellitus which is said to be one of modern diseases increasing. However, in some occasions, synthetic oral hypoglycemic agents give side effects such as serious hypoglycemia or lactic acidosis. Furthermore, synthetic oral hypoglycemic agents are not effective for juvenile diabetes mellitus. Insulin is recognized to be the most effective hypoglycemic agent. However, the use of insulin is accompanied by a diet cure and an exercise cure under strict management of a doctor, because insulin is required to be administered parenterally and has side effects such as hypoglycemia, allergy and the like. Therefore, there is a continuing need for therapeutic agents which are effective for the treatment of diabetes mellitus and which are safe and easily applicable.

SUMMARY OF THE INVENTION

Figure 1:
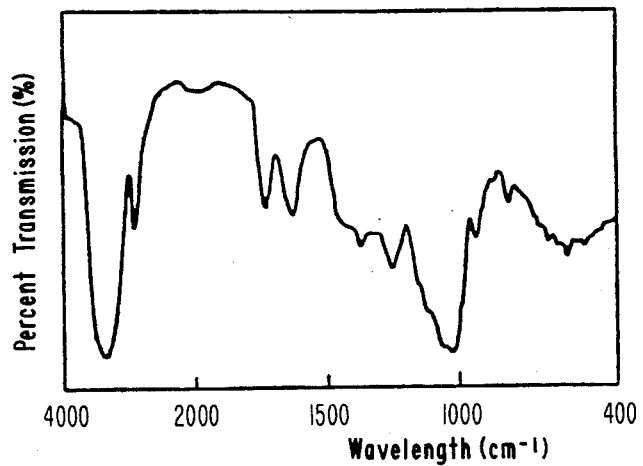
FIGS. 1 to 6 illustrate infrared spectra of A-10 to A-15 which are water extracts of Chimo and their acylated derivatives obtained in the examples.
Figure 2:
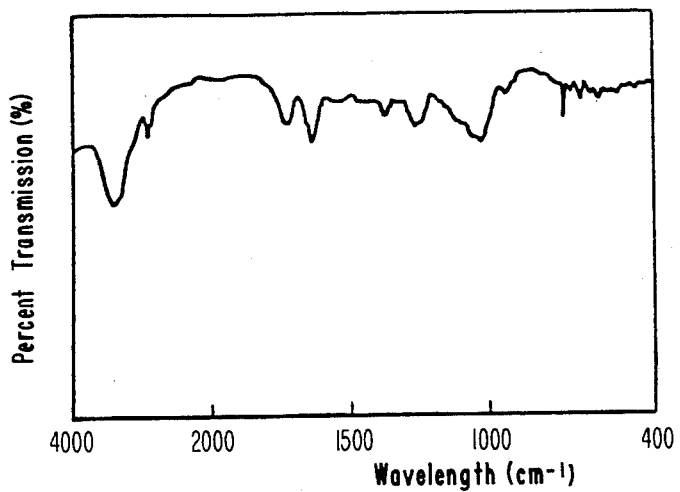
Figure 3:
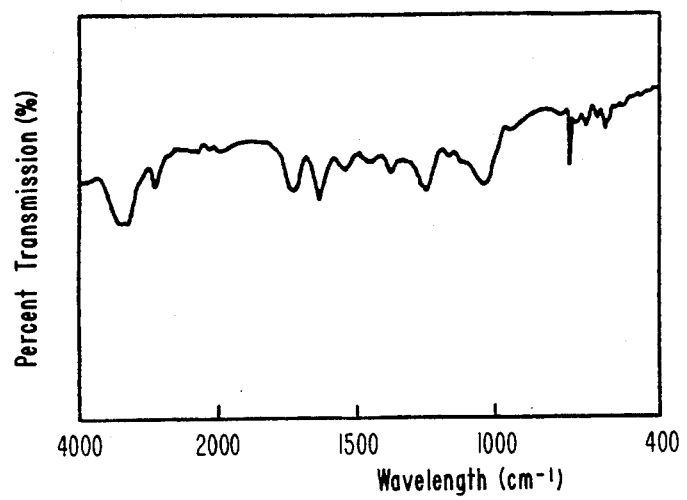
Figure 4:
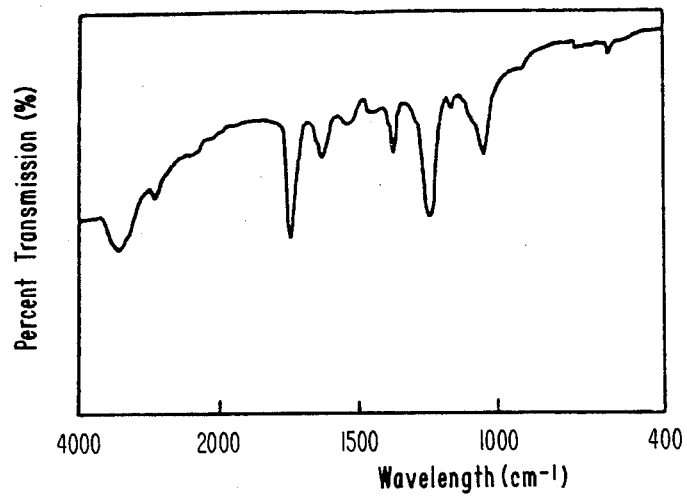
Figure 5:
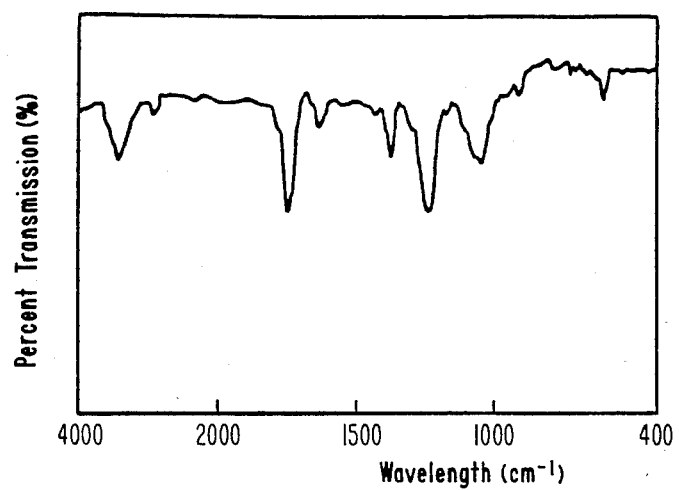
Figure 6:
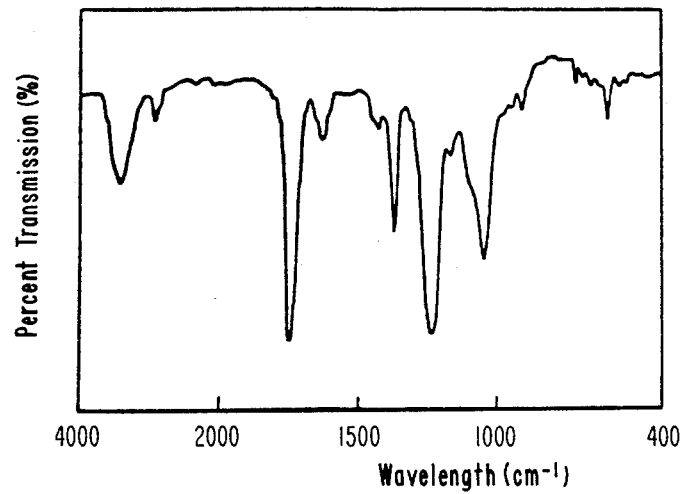

It has now been found that a novel hypoglycemic agent which is obtained from Chimo is safe and can be orally administered.

The hypoglycemic agent of this invention contains an acylated derivative of water extract of Chimo as an active ingredient, in which the acyl moiety is represented by the following formula:

wherein R is alkyl.

DETAILED DESCRIPTION OF THE PREFERRED EMBODIMENTS

The water extract of Chimo can be prepared in a conventional manner. It is preferred to remove saponins in which Chimo is rich, by means of extraction with a lower alkyl alcohol such as methanol, ethanol, propanol or butanol prior to the water extraction. As is described below, the main components of the water extract are polysaccharides. Therefore, other solvents, inorganic or organic materials may be added to the water extractant, so long a they do not give a substantial change to the water extract.

The water extraction is normally effected at room temperature, but the extraction at an elevated temperature is also possible.

In order to concentrate the active ingredients before acylation, it is preferred to remove the components of lower molecular weight. The removal of the lower molecular weight components is carried out by the usual method, for example, dialysis.

The acylation of the water extract is effected in the usual manner. For example, the water extract is acylated as follows:

Freeze-dried water extract of Chimo is acylated with a carboxylic acid anhydride or a acyl halide, such as acetic anhydride, acetyl chloride, propionyl chloride, butyryl chloride, valeryl chloride, enanthyl chloride or the like in the presence of an amine (e.g., pyridine) or an alkali. Usual post-treatment yields the desired acylated derivative. The preferred acylating agents are those having one to six carbon atoms. The kinds of amine or alkali, the amounts of reagents, or reaction conditions used in the acylation can be properly selected.

The extent of the acylation which varies with the kind of the acyl group is about 8-100%, preferably 17-66% for free hydroxyl groups present in the water extract of Chimo (the number of the hydroxyl groups is 3 per monosaccharide, when the water extract is presumed to be a polysaccharide of hexoses.).

As demonstrated in the examples, the acylated derivatives of the water extract of Chimo of this invention (hereinafter referred to as "acylated derivatives") have hypoglycemic effect and are useful as a hypoglycemic agent and an antidiabetic agent.

The acylated derivatives have no side effect such as hypoglycemia and their toxicity is very low. It is likely that the main reason for the appearance of the hypoglycemic effect of the acylated derivatives is not increment of the insulin activity but suppression of glucose absorption from digestive tract, promotion of taking glucose into muscular and fat tissues and promotion of glucose metabolism.

In addition, the acylated derivatives neither increase the amount of lactic acid in blood, nor possess a side effect such as lactic acidosis.

The acylated derivatives can be administered alone or in combination with pharmaceutically acceptable carriers, the proportion of which is determined by the solubility and chemical nature of the compound, chosen route of administration and standard pharmaceutical practice. For example, the acylated derivatives may be administered orally in the form of tablets, capsules, or granules containing suitable excipients such as starch, lactose, white sugar and the like. The acylated derivatives may be administered sublingually in the form of troches or lonzenges in which each active ingredient is mixed with sugar or corn syrups, flavoring agents and dyes, and then dehydrated sufficiently to make the mixture suitable for pressing into solid form. The acylated derivatives may be administered orally in the form of solutions which may contain coloring and flavoring agents. Physicians will determine the dosage of the present therapeutic agents which will be most suitable, and dosages vary with the particular patient under treatment.

The therapeutic dosage is generally 10-1250 mg/kg orally per day.

Having generally described this invention, a more complete understanding can be obtained by reference to certain examples which are provided herein for purposes of illustration only and are not intended to be limiting in any manner.

EXAMPLE

1. Preparation (1) Preparation of water extract of Chimo

To five hundred grams of crushed crude drug "Chimo" was added 800 g of methanol. The mixture was stirred for 7 hours at room temperature, left overnight, and then stirred for 7 hours. The extract mixture was filtered and the residue was washed with 500 g of methanol. The filtrate and the washings were combined to give the first extract solution. The residue and 1000 g of methanol were mixed and the extraction was effected with stirring in the same manner as in the first extraction above. The mixture was filtered and the residue was washed with 500 g of methanol. The filtrate and the washings were combined to give the second extract solution.

The first and second extract solutions were combined. Methanol was removed by a rotary evaporator and the extract was dried under reduced pressure by using a vacuum pump. Then, 140 g of methanol extract of Chimo was obtained. To the methanol treated residue of Chimo was added 2 l of water, and the mixture was stirred for 6 hours to give the gruel-like extract mixture. The solid portion of the mixture was separated by using a centrifuge Model KR-200A of Kubota Mfg. Co., to give the first aqueous extract layer. To the resultant extract residue was added 2 l of water, and the mixture was stirred. After 3 hours, the second aqueous extract layer was obtained by means of centrifugation. The first and second aqueous layers were combined and freeze-dried to give 109 g of water extract components.

(2) Dialysis of water extract components of Chimo

The dialysis of the above obtained freeze-dried water extract of Chimo was carried out to further concentrate the active components. A 100 g portion of the freeze-dried water extract was dissolved in 400 ml of water. A cellulose dialytic tube was packed with the above solution. Dialysis was effected for 8 hours with stirring 4 l of the outer solution. Further, the outer solution was replaced by 4 l of fresh water, and then dialysis was continued for 18 hours. The above dialysis was effected at a temperature of 4°–6° C.

The inner solution was freeze-dried to give 44 g of dialytic inner solution components. The outer solutions were combined and were freeze-dried to give 50 g of the dialytic outer solution components.

This freeze-dried inner solution was hereinafter referred to as "A-10".

The infrared spectrum of A-10 is illustrated in FIG. 1 below.

The result of elemental analysis of A-10 was as follows:

|  | C | H | N |
|---|---|---|---|
| Found | 42.42 | 6.22 | <0.3 |
| Calcd. for $(C_6H_{10}O_5)_n$ | 44.45 | 6.22 |  |

A-10 was dissolved in water and tested for anthrone-sulfuric acid reaction. The deep-blue color reaction indicates that A-10 is saccharides.

A-10 was hydrolyzed under the following conditions and the monosaccharides were determined by gas chromatography.

To 100 mg of A-10 was added 10 ml of a solution of 1N sulfuric acid-dioxan-water (1N sulfuric acid was dissolved in a dioxane-water (1:3) mixture.), and the reaction was carried out at a temperature of 80° C. for 8 hours. The reaction mixture was neutralized with 1.5N aqueous sodium hydroxide solution, and evaporated to dryness. The residue was extracted three times with 20 ml of pyridine, and the extract was evaporated to dryness. The solution which is prepared by dissolving 10 mg of mannitol in 10 ml of pyridine was added thereto as an internal standard substance. To 0.1 ml of the pyridine solution thus prepared was added 0.1 ml of trimethylsilylating (TMS) reagent.

The trimethylsilylated substances were determined by gas chromatography.

The analysis showed that 6% of D-glucose and 42% of D-mannose were formed during the hydrolysis under the above-described conditions.

(3) Preparation of the acetylated derivatives of A-10

Assuming that A-10 is a polysaccharide of $(C_6H_{10}O_5)_n$ wherein n is an integer, five different acetylated derivatives having $1n/4$, $1n/2$, $1n$, $3n/2$ and $3n$ acetyl groups per $3n$ hydroxyl groups, respectively, were synthesized and those are named as A-11, 12, 13, 14 and 15. To each of 5 eggplant type flasks was added 1.00 g of A-10 and 500 ml of dried pyridine. Then, acetyl anhydride was added slowly in an amount of 0.5 ml, 0.9 ml, 1.8 ml, 3.5 ml and 30 ml, respectively. The mixture was heated with stirring in an oil bath at 80° C. for 8 hours, while it changed from a suspension to a homogeneous mixture. Upon completion of the reaction, the pyridine-acetyl anhydride solution was subjected to reduced pressure to remove the solvent and then dissolved in chloroform. The gradual addition of n-hexan yielded a suspension containing fine particles. The suspension was filtered with suction, washed about ten-times with a few ml of n-hexane to remove pyridine thoroughly.

The fine powder obtained by filtration was dried under reduced pressure at 80° C. for 12 hours to obtain the acetyl derivatives. A-11~15. The yields of A-11~15 are shown in Table 1 below.

TABLE 1

| | Yield of A-11~15 | | |
|---|---|---|---|
| | Amount of A-10 used (g) | Amount of acetic anhydride used (ml) | Yield (g) |
| A-11 | 1.00 | 0.50 | 1.15 |
| A-12 | 1.00 | 0.90 | 1.20 |
| A-13 | 1.00 | 1.80 | 1.30 |
| A-14 | 1.00 | 3.50 | 1.21 |
| A-15 | 1.00 | 30.00 | 1.33 |

Infrared spectra of A-11~15 are shown in FIGS. 2–6, respectively.

The contents of the acetyl group in A-11~A-15 were calculated on the basis of elemental analysis data of hydrogen and integrated values of proton in $^1H_1$-n.m.r. according to the following equation. In the equation, $S_1$ represents an integrated value of proton of acetyl,

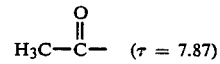

and $S_2$ represents an integrated value of proton of groups other than acetyl. ($\tau = 4.0 \sim 7.4$)

$(S_1/S_1+S_2) \times (\text{analysis of H }(\%))/1.0079) \times \frac{1}{3} \times 43.045$ The results are shown in Table 2 below.

TABLE 2

A-10 for $(C_6H_{10}O_5)_n$

|  | C | H | N |
|---|---|---|---|
| Calcd. (%) | 44.45 | 6.22 |  |
| Found (%) | 42.42 | 6.22 | <0.3 |

A-11 for $(C_{26}H_{42}O_{21})_n$

|  | C | H | N | Content of acetyl (%) |
|---|---|---|---|---|
| Calcd. (%) | 45.22 | 6.09 |  | 6.4 |
| Found (%) | 46.54 | 6.38 | <0.3 | 5.8 |

A-12 for $(C_{14}H_{22}O_{11})_n$

|  | C | H | N | Content of acetyl (%) |
|---|---|---|---|---|
| Calcd. (%) | 45.90 | 6.01 |  | 11.7 |
| Found (%) | 47.26 | 6.24 | <0.3 | 10.5 |

A-13 for $(C_8H_{12}O_6)_n$

|  | C | H | N | Content of acetyl (%) |
|---|---|---|---|---|
| Calcd. (%) | 47.06 | 5.88 |  | 20.9 |
| Found (%) | 47.37 | 5.77 | <0.3 | 20.3 |

A-14 for $(C_{10}H_{14}O_7)_n$

|  | C | H | N | Content of acetyl (%) |
|---|---|---|---|---|
| Calcd. (%) | 48.78 | 5.69 |  | 34.7 |
| Found (%) | 49.20 | 5.73 | <0.3 | 35.1 |

A-15 for $(C_{12}H_{16}O_8)_n$

|  | C | H | N | Content of acetyl (%) |
|---|---|---|---|---|
| Calcd. (%) | 50.00 | 5.56 |  | 40.3 |
| Found (%) | 48.82 | 5.56 | <0.3 | 44.5 |

2. Pharmacological Test—Hypoglycemic Effect (1) Experiments using alloxan diabetic mice Male ddY strain mice weighing 20 g on an average were used in these experiments. Alloxan diabetic mice were produced by intravenous injection of alloxan monohydrate. After two weeks from the injection, mice which had positive urinary glucose were fasted for 16 hours before experiments.

Blood samples were collected from ocular venous plexus of mice.

Blood glucose level was measured just before, and 4 hr after oral administration of each 200 mg/kg of A-11~15 (suspended in 0.5% tragacanth solution) and oral administration of 50 mg/kg of A-10 by the method described by Momose et al. (T. Momose, A. Inaba, Y. Mukai, T. Shinkai, Chem. Pharm. Bull., 8, 514 (1960)).

A control group of mice was administered orally with saline.

The results are shown in Table 3 below.

TABLE 3

| | Number of mice | blood glucose level (mg/dl) 0 time | blood glucose level (mg/dl) after 4 hrs. | Decreasing[*1] percentage (%) |
|---|---|---|---|---|
| Saline (Control) | 10 | 247.0 ± 29.1 | 182.8 ± 52.4 | 45.6 ± 31.5 |
| A-10 | 9 | 225.3 ± 25.8 | 166.6 ± 23.0 |  |
| A-11 | 9 | 243.4 ± 47.2 | 165.9 ± 52.7 | 58.2 ± 38.7 |
| A-12 | 11 | 241.1 ± 45.2 | 159.9 ± 61.9 | 67.8 ± 45.1 |
| A-13 | 11 | 241.8 ± 44.0 | 118.6 ± 52.9[*2] | 89.2 ± 40.7[*2] |
| A-14 | 9 | 225.2 ± 48.2 | 137.6 ± 67.2 | 76.2 ± 40.7 |

TABLE 3-continued

| | Number of mice | blood glucose level (mg/dl) 0 time | blood glucose level (mg/dl) after 4 hrs. | Decreasing[*1] percentage (%) |
|---|---|---|---|---|
| A-15 | 8 | 225.7 ± 19.4 | 135.3 ± 56.3 | 69.3 ± 45.3 |

[*1] Decreasing percentage = $\frac{Ci - Ct}{Ci - 100^*} \times 100$

Ci: Initial blood glucose level (mg/dl)
Ct: Blood glucose level after treatment (mg/dl)
*100 means normal level of blood glucose level (mg/dl)
The values of "blood glucose level" and "decreasing percentage" are represented as "Mean ± S.D. (standard deviation)".
[*2] $p < 0.05$ (2) Experiments using normal mice Male ddY strain mice weighing 20 g on an average were fasted for 16 hours before experiments. The collection of blood samples and their measurement were made in the same manner as described in 2-1).

Each 200 mg/kg of A-11~15 (suspended in 0.5% tragacanth solution) were administered orally. A control group of mice was administered orally with saline.

The results are shown in Table 4 below.

TABLE 4

| | Number of mice | blood glucose level (mg/dl) 0 time | blood glucose level (mg/dl) after 4 hrs. |
|---|---|---|---|
| Saline (Control) | 9 | 72.1 ± 20.8 | 88.1 ± 26.4 |
| A-11 | 9 | 72.3 ± 17.1 | 90.1 ± 14.5 |
| A-12 | 9 | 76.5 ± 14.9 | 85.2 ± 15.0 |
| A-13 | 9 | 73.4 ± 17.1 | 85.7 ± 17.2 |
| A-14 | 9 | 69.5 ± 15.0 | 86.2 ± 20.5 |
| A-15 | 9 | 63.7 ± 13.2 | 75.9 ± 15.5 |

The value of blood glucose level is represented as "Mean ± SD. (standard deviation)".

(3) Acute toxicity

Male ddY strain mice weighing 20 g on an average were administered orally with an aqueous solution of A-10 or a suspension of A-11~15 in 0.5% tragacanth solution and $LD_{50}$ value for mice was determined.

As it was impossible to administer A-11~15 in an amount of above 1250 mg/kg, $LD_{50}$ values were above 1250 mg/kg.

When 1250 mg/kg of A-11~15 were administered to seven mice, none of the mice died.

The result are shown in Table 5 below.

TABLE 5

| | Number of mice | $LD_{50}$ |
|---|---|---|
| A-11 | 7 | above 1250 mg/kg |
| A-12 | 7 | " |
| A-13 | 7 | " |
| A-14 | 7 | " |
| A-15 | 7 | " |
| A-10 | 7 | above 4000 mg/kg |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. An acylated water extract of *Anemarrhenae rhizoma* in which the acyl moiety is represented by the formula

wherein R is lower alkyl, produced by repeatedly extracting *Anemarrhenae rhizoma* first with an excess of a lower alkyl alcohol until saponin is removed and then with water to give a water extract containing polysaccharides having free hydroxyl groups as a major component thereof, subjecting the water extract to dialysis until low molecular weight components are removed, and acylating the dried water extract with a lower alkyl acid anhydride or halide until at least 8 percent of free hydroxyl groups in the dried extract are acylated.

2. The acylated extract of claim 1 wherein R is methyl.

3. A composition for the treatment of diabetes mellitus, comprising an effective amount of the acylated extract of claim 1 and a pharmaceutical acceptable carrier therefor.

4. The composition of claim 3 wherein R is methyl.